US012319912B2

(12) United States Patent
Otsuka et al.

(10) Patent No.: US 12,319,912 B2
(45) Date of Patent: Jun. 3, 2025

(54) MICRORNA EXPRESSION PROMOTING AGENT AND FOOD OR BEVERAGE FOR PROMOTING EXPRESSION OF MICRORNA

(71) Applicant: Kewpie Corporation, Tokyo (JP)

(72) Inventors: Kurataka Otsuka, Chofu (JP); Takahiro Ochiya, Tokyo (JP)

(73) Assignee: Kewpie Corporation, Tokyo (JP)

(*) Notice: Subject to any disclaimer, the term of this patent is extended or adjusted under 35 U.S.C. 154(b) by 898 days.

(21) Appl. No.: 17/436,721

(22) PCT Filed: Mar. 5, 2020

(86) PCT No.: PCT/JP2020/009481
§ 371 (c)(1),
(2) Date: Sep. 7, 2021

(87) PCT Pub. No.: WO2020/184390
PCT Pub. Date: Sep. 17, 2020

(65) Prior Publication Data
US 2022/0170014 A1 Jun. 2, 2022

(30) Foreign Application Priority Data
Mar. 8, 2019 (JP) ................ 2019-042523

(51) Int. Cl.
A23L 33/13 (2016.01)
A61K 31/712 (2006.01)
C12N 15/113 (2010.01)
C12Q 1/68 (2018.01)

(52) U.S. Cl.
CPC ............ C12N 15/113 (2013.01); A23L 33/13 (2016.08); A61K 31/712 (2013.01)

(58) Field of Classification Search
None
See application file for complete search history.

(56) References Cited

U.S. PATENT DOCUMENTS

2016/0324801 A1    11/2016  Dixon et al.
2020/0397744 A1*   12/2020  Rehman ................. A61K 31/05

FOREIGN PATENT DOCUMENTS

JP         6573740 B2       9/2019
JP         6613387 B2      11/2019
WO     2013/051459 A1       4/2013
WO     2019/049612 A1       3/2019

OTHER PUBLICATIONS

Jeyabalan et al., Journal of Agriculture and Food Chemistry vol. 62:3963-3971, 2014.*
Mak et al., (Mol. Nutr. Food Res. vol. 57:1123-1134, 2013.*
Tolba et al., Sci. Rep. 5,15239, 2015, 12 pages.*
International Preliminary Report on Patentability and Written Opinion issued in corresponding International Patent Application No. PCT/JP2020/009481 dated Sep. 23, 2021.
Dhar et al., "Resveratrol and pterostilbene epigenetically restore PTEN expression by targeting oncomiRs of the miR-17 family in prostate cancer," Oncotarget, 6 (29): 27214-27226 (2015).
Wakimoto et al., "Differential anticancer activity of pterostilbene against three subtypes of human breast cancer cells," Anticancer Research, 37: 6153-6159 (2017).
McCormack et al., "Genomic analysis of pterostilbene predicts its antiproliferative effects against pancreatic cancer in vitro and in vivo," Journal of Gastrointestinal Surgery, 16: 1136-1143 (2012).
Hagiwara et al., "Stilbene derivatives promote Ago2-dependent tumor-suppressive microRNA activity," Scientific Reports, 2: 314 (2012).
International Search Report issued in corresponding International Patent Application No. PCT/JP2020/009481 dated Apr. 21, 2020.

* cited by examiner

Primary Examiner — Sean McGarry
(74) Attorney, Agent, or Firm — Morgan, Lewis & Bockius LLP

(57) ABSTRACT

The present invention relates to a microRNA expression promoting agent, containing pterostilbene, wherein the microRNA is at least one selected from the group consisting of miR-34a, miR-16, miR-126, miR-193b, and let-7a.

11 Claims, 2 Drawing Sheets

Specification includes a Sequence Listing.

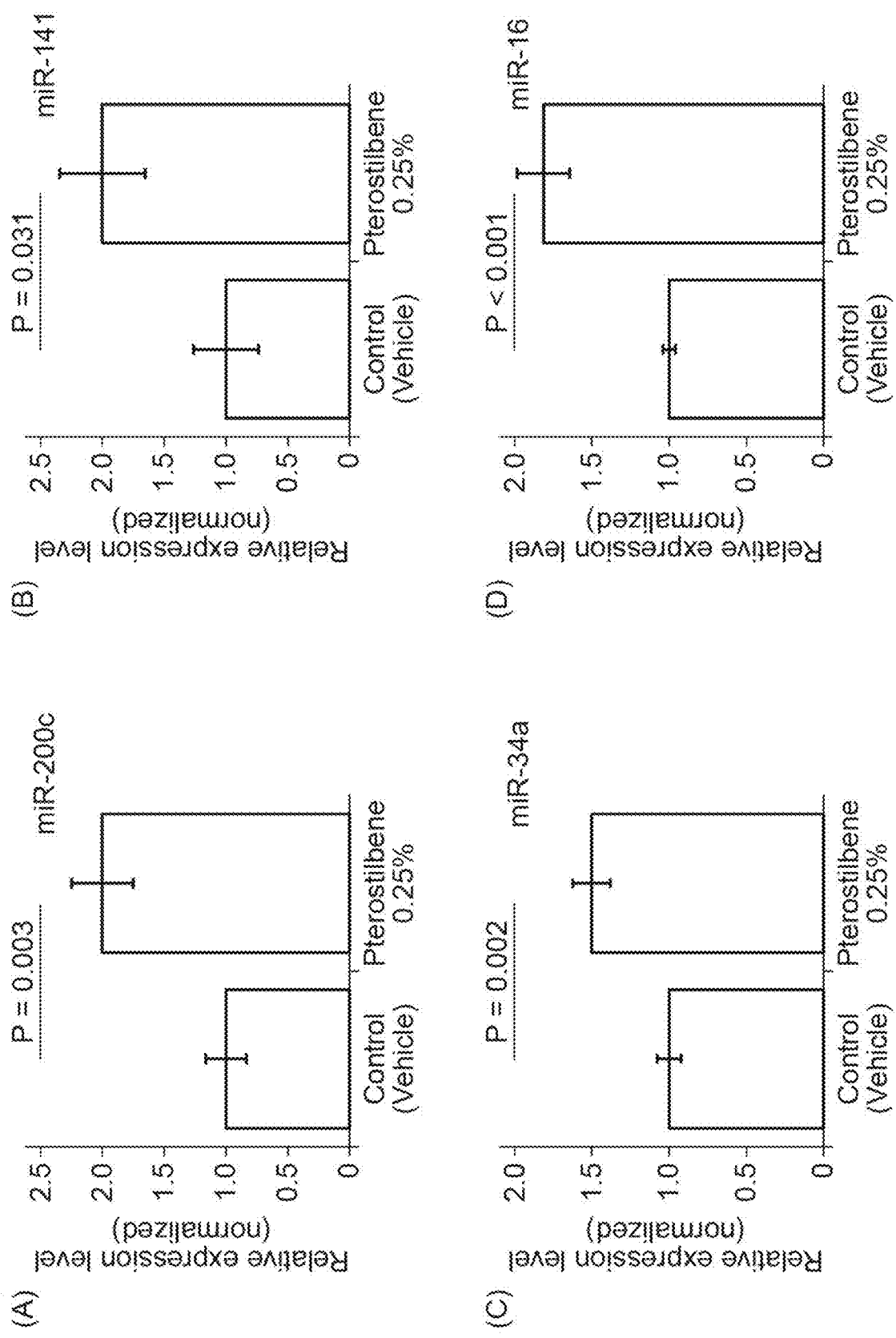

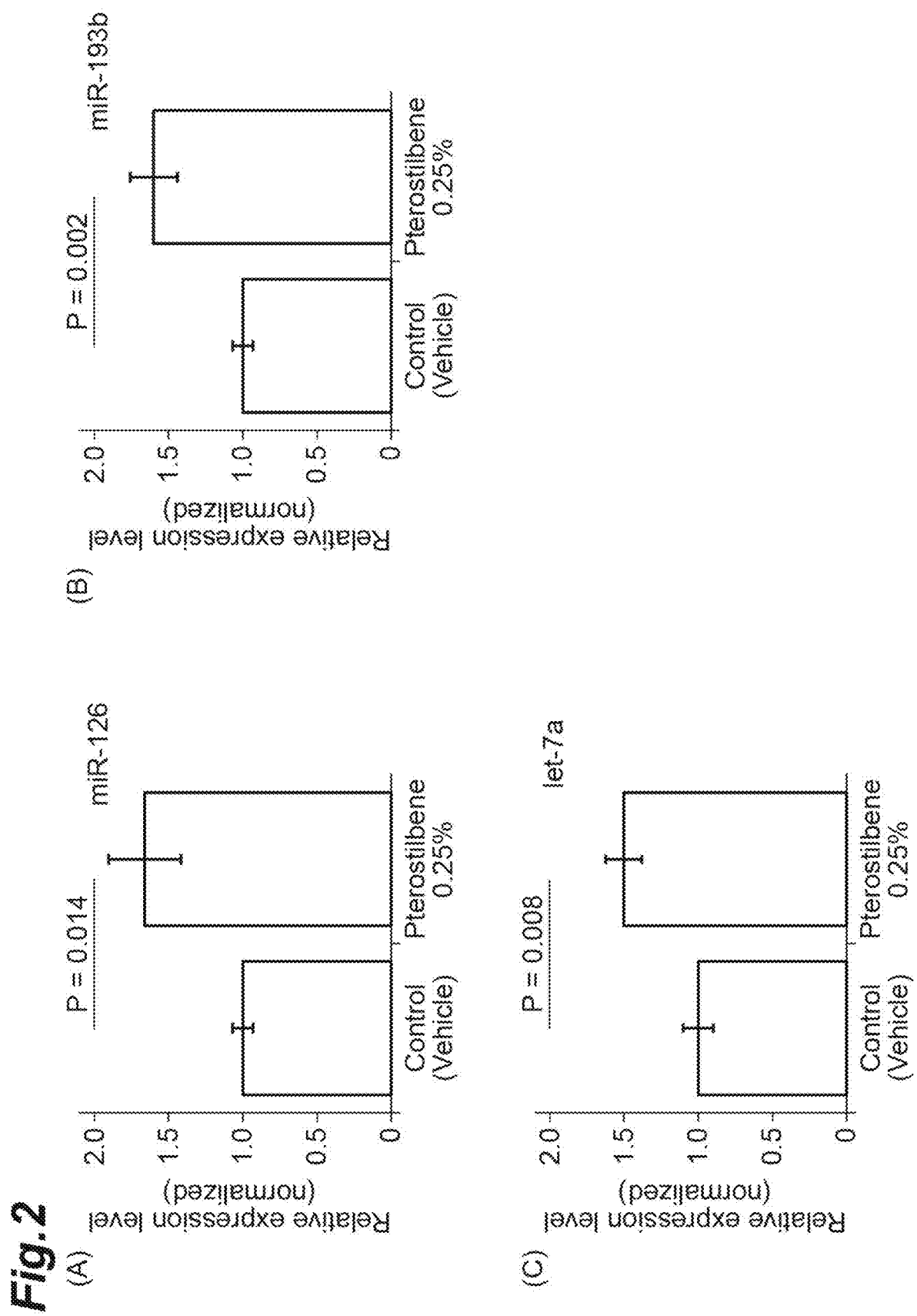

SEQUENCE LISTING

<160> NUMBER OF SEQ ID NOS: 7

<210> SEQ ID NO 1
<211> LENGTH: 23
<212> TYPE: RNA
<213> ORGANISM: Homo sapiens

<400> SEQUENCE: 1
uaauacugcc ggguaaugau gga                      23

<210> SEQ ID NO 2
<211> LENGTH: 22
<212> TYPE: RNA
<213> ORGANISM: Homo sapiens

<400> SEQUENCE: 2
uaacacuguc ugguaaagau gg                       22

<210> SEQ ID NO 3
<211> LENGTH: 22
<212> TYPE: RNA
<213> ORGANISM: Homo sapiens

<400> SEQUENCE: 3
uggcaguguc uuagcugguu gu                       22

<210> SEQ ID NO 4

<400> SEQUENCE: 4

000

<210> SEQ ID NO 5
<211> LENGTH: 22
<212> TYPE: RNA
<213> ORGANISM: Homo sapiens

<400> SEQUENCE: 5
ucguaccgug aguaauaaug cg                       22

<210> SEQ ID NO 6
<211> LENGTH: 22
<212> TYPE: RNA
<213> ORGANISM: Homo sapiens

<400> SEQUENCE: 6
aacuggcccu caaagucccg cu                       22

```
<210> SEQ ID NO 7
<211> LENGTH: 22
<212> TYPE: RNA
<213> ORGANISM: Homo sapiens

<400> SEQUENCE: 7
ugagguagua gguuguauag uu                                              22
```

MICRORNA EXPRESSION PROMOTING AGENT AND FOOD OR BEVERAGE FOR PROMOTING EXPRESSION OF MICRORNA

SEQUENCE LISTING SUBMISSION VIA EFS-WEB

A computer readable text file, entitled "SequenceListing.txt," created on Oct. 1, 2021 with a file size of about 1,263 bytes contains the sequence listing for this application and is hereby incorporated by reference in its entirety.

TECHNICAL FIELD

The present invention relates to a microRNA expression promoting agent and a food or beverage for promoting microRNA expression.

BACKGROUND ART

A microRNA is an RNA having a base pair length of about 22 bases. It is known that resveratrol and pterostilbene, which are stilbene derivatives, promote or suppress the expression of a predetermined microRNA among such microRNAs (Non Patent Literatures 1 and 2).

CITATION LIST

Non Patent Literature

Non Patent Literature 1: Scientific Reports, 2, 314, 2012
Non Patent Literature 2: Oncotarget, 2015, Vol. 6, No. 29, pp. 27214-27226

SUMMARY OF INVENTION

Problems to be Solved by the Invention

In recent years, with regard to microRNAs called miR-200c, miR-141, miR-34a, miR-16, miR-126, miR-193b, and let-7a, it has been known that there is a relationship between abnormal expression levels and the occurrence of diseases such as cancer, osteoporosis, myocardial infarction, brain diseases, circulatory diseases, cognitive impairment, and periodontal disease, and any compound capable of controlling (promoting) the expression levels of the above-described microRNAs is useful as a therapeutic agent and/or prophylactic agent for various diseases.

Thus, it is an object of the present invention to provide a novel microRNA expression promoting agent.

Means for Solving the Problems

The present invention relates to, for example, the following various inventions.
(1) A microRNA expression promoting agent, containing pterostilbene, wherein the microRNA is at least one selected from the group consisting of miR-34a, miR-16, miR-126, miR-193b, and let-7a.
(2) The expression promoting agent according to (1), wherein the expression promoting agent is for oral administration.
(3) A microRNA expression promoting agent for oral administration, containing pterostilbene, wherein the microRNA is at least one selected from the group consisting of miR-200c and miR-141.
(4) A food or beverage for promoting microRNA expression, the food or beverage containing pterostilbene, wherein the microRNA is at least one selected from the group consisting of miR-200c, miR-141, miR-34a, miR-16, miR-126, miR-193b, and let-7a.
(5) A method for promoting the expression of a microRNA, the method including administering pterostilbene to a subject in need thereof, wherein the microRNA is at least one selected from the group consisting of miR-34a, miR-16, miR-126, miR-193b, and let-7a.
(6) A method for promoting the expression of a microRNA, the method including orally administering pterostilbene to a subject in need thereof, wherein the microRNA is at least one selected from the group consisting of miR-200c and miR-141.
(7) Use of pterostilbene for the production of a microRNA expression promoting agent, wherein the microRNA is at least one selected from the group consisting of miR-34a, miR-16, miR-126, miR-193b, and let-7a.
(8) Use of pterostilbene for the production of a microRNA expression promoting agent for oral administration, wherein the microRNA is at least one selected from the group consisting of miR-200c and miR-141.
(9) Pterostilbene for use in promoting the expression of a microRNA, wherein the microRNA is at least one selected from the group consisting of miR-34a, miR-16, miR-126, miR-193b, and let-7a.
(10) Pterostilbene for use in promoting the expression of a microRNA by oral administration, wherein the microRNA is at least one selected from the group consisting of miR-200c and miR-141.

Effects of the Invention

According to the present invention, a novel microRNA expression promoting agent is provided.

BRIEF DESCRIPTION OF DRAWINGS

FIG. 1(A) to FIG. 1(D) are graphs showing the results of measuring the expression levels of miR-200c, miR-141, miR-34a, and miR-16, respectively.
FIG. 2(A) to FIG. 2(C) are graphs showing the results of measuring the expression levels of miR-126, miR-193b, and let-7a, respectively.

EMBODIMENTS FOR CARRYING OUT THE INVENTION

Hereinafter, embodiments for carrying out the present invention will be described in detail. However, the present invention is not intended to be limited to the following embodiments.

Features of Present Invention (MicroRNA Expression Promoting Agent)
The present invention has a feature of providing a microRNA expression promoting agent, containing pterostilbene, wherein the microRNA is at least one selected from the group consisting of miR-34a, miR-16, miR-126, miR-193b, and let-7a.
(MicroRNA Expression Promoting Agent for Oral Administration)
The present invention has a feature of providing a microRNA expression promoting agent for oral administration, containing pterostilbene, wherein the microRNA is at least one selected from the group consisting of miR-200c and miR-141.

(Food or Beverage)

The present invention also has a feature of providing a food or beverage for promoting microRNA expression, the food or beverage including pterostilbene, wherein the microRNA is at least one selected from the group consisting of miR-200c, miR-141, miR-34a, miR-16, miR-126, miR-193b, and let-7a.

<MicroRNA Expression Promoting Agent>

The "microRNA expression promoting agent" may be an agent that increases the level of a microRNA from a state in which the expression level of the microRNA has been lowered to an expression level similar to that of a healthy person (healthy subject) or may be an agent that maintains the expression level of the microRNA to an expression level similar to that of a healthy person. That is, the microRNA expression promoting agent can be expressed differently as a microRNA expression regulating agent, a microRNA expression control agent, or a microRNA expression enhancer.

<MicroRNA>

The expression promoting agent of the present embodiment promotes the expression of miR-200c, miR-141, miR-34a, miR-16, miR-126, miR-193b, and let-7a. Therefore, the expression promoting agent of the present embodiment can be used as an expression promoting agent of one kind or two or more kinds of the above-described microRNAs.

<Use Application of MicroRNA Expression Promoting Agent>

The expression promoting agent for the above-mentioned microRNAs can be suitably used as a therapeutic agent and/or prophylactic agent for diseases such as cancer, osteoporosis, myocardial infarction, brain diseases, circulatory diseases, cognitive impairment, and periodontal disease.

<Sequence of Each MicroRNA>

The above-mentioned microRNAs are mature single-stranded microRNAs and respectively have sequences as shown below.

```
(1) miR-200c:
                                    (SEQ ID NO: 1)
UAAUACUGCCGGGUAAUGAUGGA (2) miR-141:
                                    (SEQ ID NO: 2)
UAACACUGUCUGGUAAAGAUGG (3) miR-34a:
                                    (SEQ ID NO: 3)
UGGCAGUGUCUUAGCUGGUUGU (4) miR-16:
                                    (SEQ ID NO: 4)
UAGCAGCACGUAAAUAUUGGCG (5) miR-126:
                                    (SEQ ID NO: 5)
UCGUACCGUGAGUAAUAAUGCG (6) miR-193b:
                                    (SEQ ID NO: 6)
AACUGGCCCUCAAAGUCCCGCU (7) let-7a:
                                    (SEQ ID NO: 7)
UGAGGUAGUAGGUUGUAUAGUU
```

<Pterostilbene>

Pterostilbene is a compound represented by the following Formula (1).

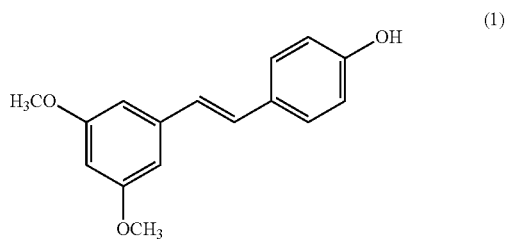 [SMILES: COc1cc(/C=C/c2ccc(O)cc2)cc(OC)c1]

<Content of Pterostilbene>

With regard to the expression promoting agent of the present embodiment, the content of pterostilbene may be 0.01% by mass or more or 0.10% by mass or more, or 10% by mass or less or 5% by mass or less, based on the total amount of the expression promoting agent.

<Method of Obtaining Pterostilbene>

According to the present embodiment, regarding pterostilbene, a commercially available product may be used, or a product obtained by chemical synthesis may be used.

<Oils and Fats>

The expression promoting agent of the present embodiment may further contain oils and fats. In this case, the expression promoting agent becomes more suitable for use in oral administration.

<Types of Oils and Fats>

The oils and fats that may be incorporated in the expression promoting agent of the present embodiment may be animal oils or may be plant oils. Examples of the oils and fats include plant oils such as corn oil, soybean oil, sesame oil, rapeseed oil, safflower oil, olive oil, castor oil, cotton seed oil, rice bran oil, sunflower oil, grape seed oil, and wheat germ oil; animal oils such as egg yolk oil, fish oil, whale oil, and liver oil; refined oils (salad oil) of these, and edible oils obtainable by applying chemical or enzymatic treatment, such as MCT (medium-chain fatty acid triglycerides) and diglycerides. Oils and fats may be used singly, or two or more kinds thereof may be used in combination.

<Content of Oils and Fats>

The content of the oils and fats may be 0.1% by mass or more or 1% by mass or more, or 10% by mass or less or 8% by mass or less, based on the total amount of the expression promoting agent.

<Additives>

The expression promoting agent of the present embodiment may further contain additives (excluding pterostilbene and oils and fats). Examples of the additives include an excipient, a binder, a lubricating agent, a disintegrant, an emulsifier, a surfactant, a base, a dissolution aid, and a suspending agent.

<Formulation>

The expression promoting agent of the present embodiment may be in any form such as a solid (for example, a powder), a liquid (a water-soluble or oil-soluble solution or suspension), or a paste. Furthermore, the expression promoting agent may be in any dosage form such as a powder preparation, a granular preparation, a tablet, a capsule, a solution, a suspension, or a syrup.

<Method for Preparing Expression Promoting Agent>

The various above-mentioned preparations can be prepared by mixing pterostilbene with the above-described oils and fats and additives as necessary, and molding the mixture as necessary.

With regard to the method for preparing a microRNA expression promoting agent, a case where the dosage form is a liquid will be described below. First, oils and fats that have been heated to a product temperature of 50° C. to 90° C. are prepared. Pterostilbene is added to the heated oils and fats and is dissolved therein. Subsequently, a mixture of pterostilbene and oils and fats is mixed with other ingredients, the mixture is subjected to a sterilization treatment or the like, as necessary, and thus a preparation containing pterostilbene can be prepared.

<Administration Method>

Since the expression promoting agent of the present embodiment can exhibit expression promoting action for the above-described microRNA when orally administered, the expression promoting agent can be used for oral administration. That is, the expression promoting agent of the present embodiment can be used as an expression promoting agent for oral administration of one kind or two or more kinds of the above-described microRNAs. Usually, a preparation that provides a desired effect by parenteral administration such as intraperitoneal administration is not considered to always provide the desired effect even by oral administration. On the other hand, the expression promoting agent of the present embodiment provides a microRNA expression promoting effect by parenteral administration and also provides a microRNA expression promoting effect even by oral administration. The amount of administration, timing for administration, and duration of administration of the microRNA expression promoting agent can be appropriately set.

<Subject of Administration>

A biological body that is a subject of administration of the expression promoting agent of the present embodiment is preferably a mammal, and more preferably a human being.

<Amount of Administration>

As a specific example of the amount of administration, for example, in the case of administering the expression promoting agent to a human male adult (body weight 60 kg), the amount of administration of the expression promoting agent per day may be 0.01 mg to 5000 mg/day/person, and the amount of administration is 0.05 mg to 1000 mg/day/person, more preferably 0.1 mg to 500 mg/day/person, and even more preferably 0.5 mg to 250 mg/day/person. Regarding the expression promoting agent, when the amount of administration per day is in the above-described range, the expression promoting agent may be administered once a day or may be dividedly administered several times (for example, 2 times or 3 times) a day. Incidentally, the amount of administration is a value based on the amount of an active ingredient (that is, pterostilbene) in the expression promoting agent.

<Use Application of Expression Promoting Agent>

The expression promoting agent of the present embodiment can be used as an ingredient of manufactured products such as pharmaceutical products, quasi-drugs, foods and beverages (beverages and foods), animal feeds, and feed additives. Examples of the beverages include water, soft drinks, fruit juice beverages, milk beverages, alcohol beverages, sports drinks, and nutritional drinks. Examples of the foods include breads, noodles, rice, tofu, dairy products, soy sauce, miso paste, confectionery, creams, sauces, mayonnaise, and dressings. Furthermore, the expression promoting agent of the present embodiment can also be used as an ingredient of health foods, foods with functional claims, foods of special purpose, dietary supplements, supplements (for example, doctor's supplements), or foods for specified health use.

<Food or Beverage for Promoting MicroRNA Expression>

The expression promoting agent of the present embodiment can be used as an ingredient of a food or a beverage. That is, as an embodiment of the present invention, there is provided a food or beverage (food composition) for promoting microRNA expression containing pterostilbene, wherein the microRNA is at least one selected from the group consisting of miR-200c, miR-141, miR-34a, miR-16, miR-126, miR-193b, and let-7a.

<Method of Promoting Expression of MicroRNA>

An embodiment of the present invention may also be regarded as a method of promoting the expression of a microRNA, the method including administering pterostilbene to a subject in need of the compound. With regard to this method, the administration method, subject of administration, amount of administration, and the like may be similar to those mentioned in connection with the above-described expression promoting agent. The subject is preferably a mammal, and more preferably a human being.

<Use of Pterostilbene for Production of Expression Promoting Agent>

As an embodiment of the present invention, use of pterostilbene for the production of a microRNA expression promoting agent is provided. Incidentally, the administration method, subject of administration, amount of administration, and the like according to this embodiment may be similar to those mentioned in connection with the above-described expression promoting agent.

<Pterostilbene for Use in Promoting Expression of MicroRNA>

As an embodiment of the present invention, there is provided pterostilbene for use in promoting the expression of a microRNA. Incidentally, the administration method, subject of administration, amount of administration, and the like according to this embodiment may be similar to those mentioned in connection with the above-described expression promoting agent.

EXAMPLES

Hereinafter, the present invention will be described more specifically based on Examples and the like. However, the present invention is not intended to be limited to the following Examples.

(Statistical Analysis)

In the following Examples, a statistical analysis was carried out such that an analysis of variance (One-Way ANOVA) was performed using Kaleida Graph 4.5 (HU-LINKS Inc.), and then the results were tested by multiple comparison (Tukey's HSD Test).

Test Example 1: Evaluation of Expression Level of MicroRNA (Reagents for Powdery Animal Feed)

The following reagents were used for the preparation of a powdery animal feed for test.

Casein (Oriental Yeast Co., Ltd.)
  DL-methionine (Wako Pure Chemical Industries, Ltd.)
  β-cornstarch (Oriental Yeast Co., Ltd.)
  Sucrose (KH1 pure caster sugar) (WADA SUGAR REFINING CO., LTD.)
  Cellulose powder (Oriental Yeast Co., Ltd.)
  Corn oil (corn germ-bran oil) (J-Oil Mills, Inc.)
  Mineral mix (AIN-93G mineral mix) (Oriental Yeast Co., Ltd.)

Vitamin mix (AIN-93 vitamin mix) (Oriental Yeast Co., Ltd.)

Choline bitartrate (Wako Pure Chemical Industries, Ltd.) (Lot. No.: PDQ0575, CTK0241)

90% Pterostilbene (Silbinol) (manufactured by Sabinsa Japan Corporation)

(Preparation of Pterostilbene-Containing Powdery Animal Feed)

An animal feed for test (pterostilbene-containing powdery animal feed) was prepared by the following method. That is, first, 50 g of corn oil was weighed and heated to 70° C. Pterostilbene was added to the heated corn oil and was dissolved therein. Reagents other than corn oil and pterostilbene (other reagents) were ground in a mortar, and the mixture was mixed. The corn oil in which pterostilbene was dissolved was added to the mixture of other reagents, and the mixture was mixed by sufficiently grinding in a mortar. Subsequently, the mixture was further mixed with a stirrer for about 30 minutes, and thus an animal feed for test was prepared. The composition of the various ingredients included in the animal feed for test is as shown in Table 1. The animal feed for test was placed in a plastic bag and was subjected to gamma-ray sterilization with KOGA ISOTOPE, Ltd., and then the animal feed for test was used for the animal experiment that will be described below. Furthermore, an acclimatization diet having the composition indicated in Table 1 (content of pterostilbene: 0% by mass) was prepared.

TABLE 1

| Unit: mass % | Acclimatization diet | Pterostilbene-containing powdery animal feed 0.25% (w/w) |
|---|---|---|
| Casein | 20 | 20 |
| β-cornstarch | 15 | 15 |
| Sucrose | 50 | 49.75 |
| Cellulose | 5 | 5 |
| Mineral mix | 3.5 | 3.5 |
| Vitamin mix | 1 | 1 |
| Methionine | 0.3 | 0.3 |
| Choline tartrate | 0.2 | 0.2 |
| Corn oil | 5 | 5 |
| Pterostilbene | 0 | 0.25 |
| Total | 100 | 100 |

(Test Animal)

Regarding test animals, 5-week-old female nude mice (BALB/c-nu/nu, CAnN.Cg-Foxn1<nu>/CrlCjlj) (CHARLES RIVER LABORATORIES JAPAN, INC.) were used.

(Reagents)

Regarding reagents, the following reagents were used.

ECM Gel from Engelbreth-Holm-Swam murine sarcoma (Invitrogen)

ESCAIN (registered trademark) inhalation anesthetic (Pfizer, Inc.)

Beetle Luciferin, Potassium Salt (Promega Corporation)

Propylene glycol (Sigma-Aldrich Inc.)

(Breeding Method)

The above-described test animals were bred in an environment maintained under the conditions of a temperature of 20° C. to 25° C. and a humidity of 40% to 60%. As a feeder, a hanging type feeder was used.

(Test Group)

Two groups of test sections of (i) a control group (0% (w/w) pterostilbene group, n=18) and (ii) 0.25% (w/w) pterostilbene (n=18), each group including eight animals or ten animals, were set.

(Testing Method and Evaluation Results)

First, 5-week-old female nude mice were acclimatized to the environment for about one week before initiating the experiment.

Regarding an examination of the influence of oral administration of the pterostilbene-containing powdery animal feed on the expression level of a microRNA, first, the animals were given a control diet (acclimatization diet) in a hanging type feeder for about one week, and then the animals were grouped into two groups of (i) control group and (ii) 0.25% (w/w) pterostilbene group. The control group was fed by orally administering the acclimatization diet, and the pterostilbene group was fed by orally administering the pterostilbene-containing powdery animal feed (content of pterostilbene: 0.25% by mass).

At a time point where one week had passed after grouping, the mice in each group were subjected to a cancer cell transplantation experiment. In the cancer cell transplantation experiment, first, cancer cells to be transplanted (MM-231-luc-D3H2LN) were suspended in phosphate buffered saline (PBS), the suspension was mixed with Matrigel (ECM Gel from Engelbreth-Holm-Swammurine sarcoma) at a ratio of 1:1, and thus a suspension for transplantation (number of cells: $1 \times 10^5$ cells/ml) was prepared. Next, under anesthesia using isoflurane (ESCAIN (registered trademark) inhalation anesthetic), $1 \times 10^4$ cells of the cancer cells were transplanted (100 μl of the above-described suspension for transplantation (number of cells: $1 \times 10^5$ cells/ml) was introduced) into the mammary glands of the mice. Confirmation of whether the cancer cells were transplanted was achieved by leaving the animals for a while after transplantation, intraperitoneally administering a 15 mg/ml luciferin solution (Beetle Luciferin, Potassium Salt, Promega Corporation) in an amount of 150 mg/kg, and measuring cell-derived luminescence (luciferase activity) with IVIS Spectrum (PerkinElmer, Inc.) after about 10 minutes. The animal feed for test and the condition of the mice were appropriately managed daily. The body weights of the mice were measured in a timely manner. The day of administration initiation (day 0) was defined as the day when the cancer cells (tumor) were transplanted. Then, luminescence was observed over time with IVIS spectrum every other week from the day of administration initiation.

At a time point where 21 days had passed from the initiation of administration, the tumors were removed under anesthesia with isoflurane, and the mice were euthanized. The tumors removed from each group (control group or pterostilbene group) were used as specimens for measurement, and a quantitative analysis of the expression levels of miR-200c, miR-141, miR-34a, miR-16, miR-126, miR-193b, and let-7a was performed by the method that will be described below. Incidentally, in the present test example, an independent test was repeated twice.

First, RNA was extracted from the specimens for measurement using miRNeasy (registered trademark) Mini Kit according to a protocol recommended by the manufacturer.

The extracted RNA was converted to complementary DNA (cDNA) using TaqMan (registered trademark) MicroRNA assay and TaqMan (registered trademark) MicroRNA Reverse Transcription Kit, respectively according to a protocol recommended by the manufacturer. That cDNA was used as a template, and a quantitative analysis of the miRNAs was performed using TaqMan (registered trademark) Universal PCR Master Mix and NoAmpErase (registered trademark) UNG by means of StepOne Plus™ Real-Time PCR System (AppliedBiosystems). The results are shown in FIG. 1 and FIG. 2. In FIG. 1 and FIG. 2, the error bars represent standard errors.

(Evaluation Results)

As shown in FIG. 1 and FIG. 2, in the group to which pterostilbene was orally administered (pterostilbene group), the expression of miR-200c, miR-141, miR-34a, miR-16, miR-126, miR-193b, and let-7a was promoted as compared to the control group.

The invention claimed is:

1. A method for promoting the expression of a microRNA, comprising:
   administering pterostilbene to a subject in need thereof,
   wherein the microRNA is at least one selected from the group consisting of miR-34a, miR-16, miR-126, miR-193b, and let-7a,
   wherein the pterostilbene is administered in an amount effective to increase the expression level of the microRNA from a state in which the expression level of the microRNA has been lowered to an expression level of a healthy subject.

2. The method according to claim 1, wherein the pterostilbene is administered by oral administration.

3. The method according to claim 1, wherein the subject is a human subject.

4. The method according to claim 1, wherein the subject is suffering from cancer, osteoporosis, myocardial infarction, a brain disease, a circulatory disease, cognitive impairment, or periodontal disease.

5. A method for promoting the expression of a microRNA, comprising:
   administering pterostilbene to a subject in need thereof,
   wherein the microRNA is at least one selected from the group consisting of miR-34a, miR-16, miR-126, miR-193b, and let-7a,
   wherein the pterostilbene is administered in an amount effective to maintain the expression level of the microRNA to an expression level of a healthy person by administering pterostilbene.

6. A method for promoting the expression of a microRNA, comprising:
   administering pterostilbene to a subject in need thereof,
   wherein the microRNA is at least one selected from the group consisting of miR-34a, miR-16, miR-126, miR-193b, and let-7a,
   wherein the subject is suffering from osteoporosis, myocardial infarction, a brain disease, a circulatory disease, cognitive impairment, or periodontal disease.

7. A method for promoting the expression of a microRNA, comprising:
   orally administering pterostilbene to a subject in need thereof,
   wherein the microRNA is at least one selected from the group consisting of miR-200c and miR-141,
   wherein the pterostilbene is administered in an amount effective to increase the expression level of the microRNA from a state in which the expression level of the microRNA has been lowered to an expression level of a healthy subject.

8. The method according to claim 7, wherein the subject is a human subject.

9. The method according to claim 7, wherein the human subject is suffering from cancer, osteoporosis, myocardial infarction, a brain disease, a circulatory disease, cognitive impairment, or periodontal disease.

10. A method for promoting the expression of a microRNA, comprising:
    orally administering pterostilbene to a subject in need thereof,
    wherein the microRNA is at least one selected from the group consisting of miR-200c and miR-141,
    wherein the pterostilbene is administered in an amount effective to maintain the expression level of the microRNA to an expression level of a healthy person by administering pterostilbene.

11. A method for promoting the expression of a microRNA, comprising:
    orally administering pterostilbene to a subject in need thereof,
    wherein the microRNA is at least one selected from the group consisting of miR-200c and miR-141,
    wherein the human subject is suffering from osteoporosis, myocardial infarction, a brain disease, a circulatory disease, cognitive impairment, or periodontal disease.

* * * * *